Figure 1:
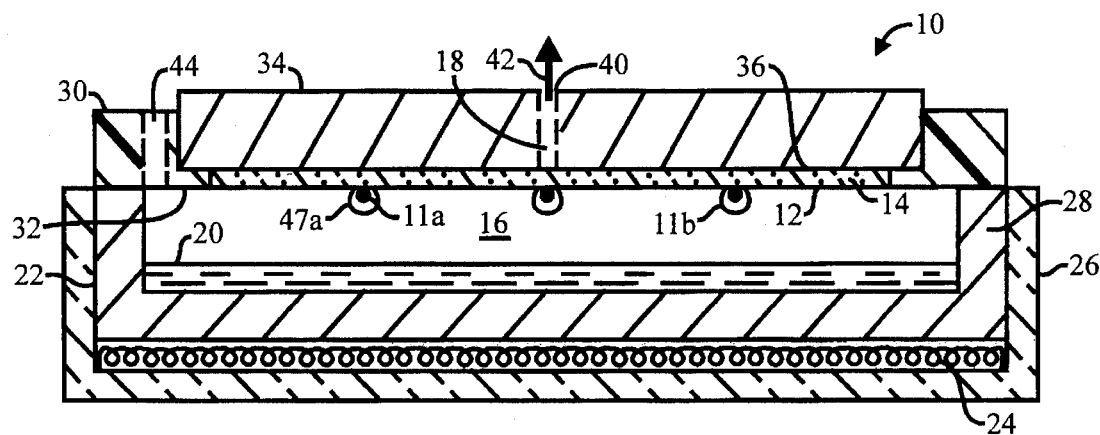

United States Patent [19]

Ye et al.

[11] Patent Number: 5,608,155
[45] Date of Patent: Mar. 4, 1997

[54] METHOD AND APPARATUS FOR DETECTING PARTICLES ON A SUBSTRATE

[75] Inventors: Yan Ye, Cupertino; Anand Gupta, San Jose, both of Calif.

[73] Assignee: Applied Materials, Inc., Santa Clara, Calif.

[21] Appl. No.: 496,946

[22] Filed: Jun. 30, 1995

Related U.S. Application Data

[63] Continuation of Ser. No. 56,332, Apr. 30, 1993, abandoned.

[51] Int. Cl.$^6$ .................................................. G01N 21/88
[52] U.S. Cl. ............................................................ 73/28.01
[58] Field of Search .............................. 73/865.5, 28.01; 356/37, 38, 335, 336, 438, 439; 250/222.2; 165/110

[56] References Cited

U.S. PATENT DOCUMENTS

| | | |
|---|---|---|
| 3,699,034 | 10/1972 | Lins et al. . |
| 3,767,306 | 10/1973 | Mast et al. . |
| 3,953,792 | 4/1976 | Fletcher et al. . |
| 4,377,340 | 3/1983 | Green et al. .......................... 356/237 |
| 4,893,932 | 1/1990 | Knollenberg .......................... 356/369 |
| 4,911,812 | 3/1990 | Kudo et al. . |
| 4,950,073 | 8/1990 | Sommer . |
| 4,967,095 | 10/1990 | Berger et al. .......................... 356/37 |
| 4,996,078 | 2/1991 | Langowski . |
| 5,023,452 | 6/1991 | Purcell et al. . |
| 5,026,155 | 6/1991 | Ockovic et al. . |
| 5,039,376 | 8/1991 | Zukotynski et al. . |
| 5,041,311 | 8/1991 | Tsukune et al. . |
| 5,068,002 | 11/1991 | Monroe . |
| 5,072,626 | 12/1991 | Ensor et al. . |
| 5,102,496 | 4/1992 | Savas . |

FOREIGN PATENT DOCUMENTS

| | | |
|---|---|---|
| 3632400A1 | 3/1988 | Germany . |
| 5003238 | 1/1993 | Japan . |

OTHER PUBLICATIONS

European Patent Office Communications, dated Aug. 3, 1994.
Bowling, R. Allen, et al., "Status and Needs of *In–Situ* Real–time Process Particle Detection," *The Journal of Environmental Sciences*, Jan./Feb. 1989, pp. 22–27.

*Primary Examiner*—Robert Raevis
*Attorney, Agent, or Firm*—Ashok K. Janah; Raymond K. Kwong

[57] ABSTRACT

The apparent size of sub-micron contaminant particles on a wafer surface is enlarged by selective condensation of a vapor on the particles. The substrate is located proximate to and spaced apart from a liquid vapor source which is heated. The vaporized liquid adheres to the particles, and after a predetermined period of time, condensation of vapor on the substrate is stopped, and the substrate is scanned for detecting the particles.

39 Claims, 1 Drawing Sheet

METHOD AND APPARATUS FOR DETECTING PARTICLES ON A SUBSTRATE

This is a continuation of application Ser. No. 08/056,332 filed on Apr. 30, 1993, now abandoned.

BACKGROUND

The present invention is directed to a method and apparatus useful for detecting sub-micron sized particles on a substrate.

Particulate contamination of semiconductor wafers during processing of the wafer is a serious problem. Semiconductor devices, such as integrated circuit chips, have micron and sub-micron sized features. Deposition of sub-micron sized contaminant particles, such as dust, on these features during processing of the wafer can render the integrated circuits on the wafer nonfunctional. Consequential, semiconducting wafers are processed in clean rooms to minimize deposition of contaminant particles on the substrate surfaces.

Even with processing in ultra clean environments, sub-micron sized contaminant particles can still deposit on the substrates during processing. Thus, it is important to nondestructively detect these contaminant particles during the initial stages of fabricating the integrated circuit chip. Failure to detect the contaminant particles until the final stages of the manufacturing process, results in the loss of a wafer, which at this stage may be worth as much as $50,000 to $100,000. Scrapping wafers due to particle contamination is very costly.

Conventional techniques, such as laser scanning, allow detection of particles sized larger than about 0.1 micron. Laser scanning techniques detect and measure the scattering of a laser beam which is scanned over the surface of the substrate. The laser beam is scattered by the contaminant particles on the substrate surface. However, such techniques are of limited value for detecting particles which are sized smaller than 0.1 micron.

Accordingly, there is a need for methods and apparatus for nondestructively detecting sub-micron sized contaminant particles on the surfaces of semiconductor substrates.

SUMMARY

The present invention satisfies this need. The apparatus enlarges the apparent size of sub-micron sized particles on the substrate surface so that the particles can be detected by conventional scanning techniques.

An enlarging apparatus according to the present invention comprises a condensation chamber or zone, a holder for holding a substrate in the chamber, and a vapor source for providing vapor in the condensation chamber for contacting the surface of the substrate having particles thereon. The apparatus also includes means for maintaining the substrate surface at or below the dew point of the vapor, so that condensate is selectively formed on particles on the substrate surface, without condensate forming on the entire surface of the substrate. The condensate serves to enlarge the apparent size of the contaminant particles, so that the particles can be detected by a scanning device.

The present invention is also directed to a method for detecting particles comprising contacting the surface of the substrate with a vapor, and selectively condensing vapor to form condensate on particles on the substrate surface by maintaining the surface of the substrate at a temperature up to the dew point of the vapor. Condensation of vapor on the surface is stopped before the entire surface of the substrate has condensate thereon, and the particles with their apparent size enlarged, are then detected.

The vapor can be formed by heating a liquid vapor source such as glycerin, and the condensate on the particles can be formed by maintaining the substrate at room temperature, such as with a heat sink in contact with the substrate.

DRAWING

Figure 2:
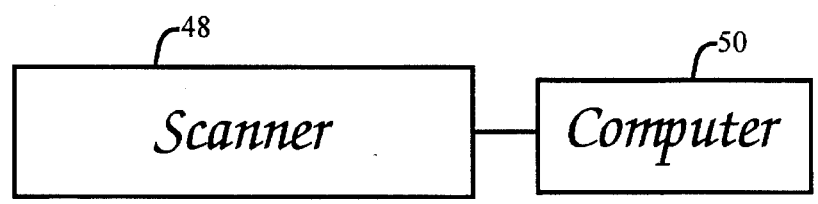
Figure 2:
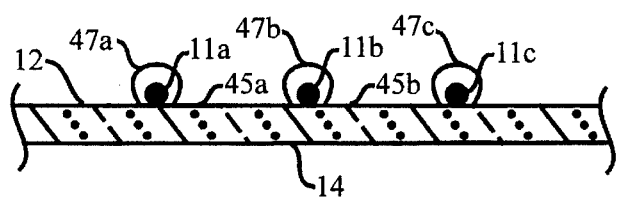

FIG. 1 is a diagrammatic side view of an apparatus embodying features of the present invention for forming condensate on sub-micron particles on a substrate; and FIG. 2 is a schematic view of a scanning system for detecting the enlarged particles formed by the apparatus of FIG. 1.

DESCRIPTION

The present invention is directed to an apparatus 10 for enlarging the apparent size of particles 11 on a lower surface 12 of a substrate 14 for facilitating detection of particles 11. The apparatus comprises a condensation chamber 16, a holding mechanism 18 for holding the substrate 14 in the condensation chamber 16, and a vapor source 20 providing vapor in the condensation chamber 16, the vapor contacting the lower surface 12 of the substrate 14.

The apparatus 10 comprises a metal container 22 that contains the vapor source 20 which is typically a vaporizable liquid. Below the metal container 22 is a heater 24 for heating the vapor source 20. Preferably the container 22 is surrounded by an insulating member 26 for maintaining the vapor source 20 at a desired temperature.

The container 22 has an upwardly projecting peripheral lip 28 upon which an annular plastic top 30 is mounted. The top 30 has a inwardly projecting support lip 32 for horizontally supporting a lid 34. The lid 34 is preferably formed of a heat conductive material such as metal, and is placed in direct contact with an upper surface 36 of the substrate 14, to serve as a heat sink for maintaining the temperature of the substrate 14.

Conditions are maintained in the condensation chamber 16 so that vapor from the vapor source 20 condenses on the lower surface 12 of the substrate 14. In the version of the invention shown in FIG. 1, this is effected by heating the liquid vapor source 20 with the heater 24 while maintaining the substrate 14 at a temperature of up to the dew point of vapor in the condensation chamber 16. By "up to," it is meant at a temperature at or below the dew point of the vapor. Preferably, the temperature of the substrate 14 is maintained at about the dew point of the vapor. By "dew point" it is meant the temperature at which the vapor will selectively condense on and around the particles 11 on the substrate surface 12. The substrate 14 can be cooled for this purpose, or as shown in FIG. 1, the substrate can be maintained at about room temperature by being in contact with the metallic lid 34, which serves as a heat sink.

The substrate 14 is held in place and maintained in intimate contact with the lid 34 by pulling a vacuum on the substrate 14 through a vacuum port 40 in the lid 34, in the direction shown by arrow 42. The vacuum through the port 40 serves as the holding mechanism 18 for holding the substrate 14 in the chamber 16. Thus, the substrate 14 is horizontally supported in the condensation chamber 16, so that the substrate 14 is above and spaced apart from the vapor source 20. This arrangement exposes the lower surface 12 of the substrate 14, upon which the sub-micron particles 11 can exist, to the vapor generated by the vapor source 20.

The plastic top 30 is provided with a vent port 44 so that a selected amount of vapor can escape from the condensation chamber 16 for controlling the rate at which condensate forms on the substrate lower surface 12.

To use the apparatus 10, the lid 34 is placed on the lip 32 of top 30, and the substrate 14 is held to the lid 34 by pulling a vacuum through the port 40 of the lid 34. Vapor is formed in the condensation chamber 16 by heating the liquid vapor source 20, and some of the vapor condenses on the substrate lower surface 12. Because substrate lower surface 12 is horizontally oriented and because the entire substrate lower surface 12 is exposed to vapor, condensate forms on the substrate. The condensate forms on and around the particles 11 on the substrate 14 which serve as nuclei for the condensate droplets.

The substrate 14 is exposed to the vapor a sufficient time that condensate selectively forms on the particles 11, but not such a long time that condensate forms on the entire surface 12 of the substrate 14. The rate at which condensate forms on the particles 11 increases as the temperature of the substrate 14 is lowered below the dew point of the vapor, and the rate decreases as the temperature of the vapor is increased. The condensation rate also increases as the amount of vapor in the chamber 16 is reduced by opening the vent 44. Lower condensation rates are preferred so that condensation can be stopped before condensate forms on the entire substrate surface 12. Thus, the temperature of the substrate 14 is preferably maintained at or just below the dew point of the vapor.

Condensation of the vapor on the lower surface 12 is stopped after condensate forms on at least some of the particles 11 which are sized less than 0.1 micron in diameter, and before the condensate forms in the interstices 45 between the particles 11. The condensation may be stopped by removing the substrate 14 from the chamber after a certain time. The amount of time allowed for condensation is predetermined and selected according to the requisite operating parameters. If insufficient time is provided for condensation, the condensation can be extended, thus, the process can proceed in multiple stages. By using multiple stages, with intermittent particle detection steps, it is also possible to classify the particles by size because condensate first forms on the larger particles 11, and at later stages forms on the smaller particles 11.

The amount of time used to form condensate on the particles 11 for enlarging the apparent size of the particles 11 is preferably less than one minute, and typically less than 30 seconds.

The substrate 14, on being removed from the chamber, can be scanned to detect the apparently enlarged condensate droplets 47, in a scanner apparatus 48, as shown in FIG. 2. A computer 50 can control the scanner and can record the number, location, time, and size of the particles 11. A suitable scanner is a "TENCOR" (Trademark) wafer surface scanner available from Tencor, Inc., of Mountain View, Calif. These scanners operate by moving the wafer under a laser beam, so that the laser beam scans the wafer surface, and by detecting the scattering of the laser beam by the particles on the wafer surface.

The present invention is useful with a variety of substrates. It is particularly adapted for use with substrates employed in the fabrication of integrated circuits, such as silicon or gallium arsenide wafers, which generally have deposited films thereon. The substrate can also be made of polymeric, ceramic or metallic materials. The apparatus and method are effective for sub-micron particles, including particles with diameter less than 0.1 microns.

The vapor source can be any one of a variety of materials, and is typically a liquid such as isopropanol, ethanol, glycerin, or water. The vapor source can also be vaporizable solid, or a semisolid such as grease or wax. Preferably the vapor source 20 has a low vapor pressure at room temperature, and has sufficiently high surface tension that it forms a spherical condensate droplet 47 on the particles 11 on the substrate surface 12.

Rather than having the enlargement apparatus 10 separate from the scanner 48, the scanning and particle enlargement can be effected in a single apparatus. This has the advantage that the substrate 14 need not be removed from the enlargement apparatus 10, thereby avoiding problems of moving or changing the size of the condensate droplets prior to their detection.

The present invention has significant advantages. It allows for nondestructive testing of silicon wafers and other substrates so that particle contamination can be easily detected and determined early in the manufacturing process. All that is necessary is to enlarge the apparent size of sub-micron sized particles by condensing vapor on the particles, with the vapor selected so as not to adversely affect the properties of the substrate. The presence or absence of particles can be then detected with existing scanning equipment. Thus, retrofitting is not required, and capital investment in new, expensive and esoteric scanning equipment is not necessary.

Although the present invention has been described in considerable detail with reference to certain preferred versions thereof, other versions are possible. For example, in an alternate embodiment of the invention, the substrate can be cooled to a temperature at or below room temperature, with or without heating of the vapor source 14. Cooling of the substrate can be effected by cooling the lid 34. Therefore the scope of the appended claims should not be limited to the description of the preferred versions contained herein.

What is claimed is:

1. A method for detecting particles on a surface of a substrate comprising the steps of:

(a) exposing the entire surface of the substrate to a vapor by placing the substrate in a condensation zone;

(b) selectively condensing the vapor to form condensate on substantially all the particles on the substrate surface by holding a sufficiently large portion of the substrate in contact with a heat sink using a vacuum port, to maintain substantially the entire surface of the substrate at temperatures up to the dew point of the vapor;

(c) stopping condensation of vapor on the substrate surface before the entire surface of the substrate has condensate thereon by removing the substrate from the condensation zone; and (d) detecting the particles with condensate thereon on the substrate surface.

2. The method of claim 1 wherein the step of exposing the entire surface of the substrate to a vapor comprises heating a liquid to above room temperature to form the vapor, and wherein the step of selectively condensing the vapor comprises maintaining the substrate surface at a temperature of about room temperature.

3. The method of claim 2 wherein the step of maintaining the substrate surface at about room temperature comprises exposing the heat sink to room temperature.

4. The method of claim 1 wherein the step of selectively condensing comprises cooling the substrate to about room temperature.

5. The method of claim 4 herein the step of contacting the surface of the substrate with a vapor comprises heating a liquid to a temperature higher than room temperature.

6. The method of claim 1 wherein the step of stopping condensation of the vapor on the substrate surface comprises removing the substrate from contact with the vapor.

7. The method of claim 1 wherein the step of stopping condensation of vapor comprises stopping condensation after condensate forms on at least some of the particles which are less than 0.1 micron in diameter, and before condensate forms in the interstices between the particles.

8. The method of claim 1 where the step of detecting comprises detecting particles less than 0.1 micron in diameter.

9. The method of claim 8 where the step of detecting comprises detecting by laser scanning.

10. The method of claim 1 wherein the substrate comprises a silicon wafer.

11. The method of claim 10 wherein the substrate has at least one deposited film thereon.

12. The method of claim 1, wherein in step (a), the entire surface of the substrate is exposed to the vapor simultaneously.

13. The method of claim 1, wherein in step (a), more than one portion of the substrate is exposed to the vapor simultaneously.

14. A method for detecting sub-micron size particles on a surface of a substrate comprising the steps of:

(a) placing the substrate in a condensation zone;

(b) introducing vapor into the condensation zone;

(c) holding the substrate against the heat sink using a vacuum port to contact a sufficiently large portion of the substrate against the heat sink to maintain substantially the entire surface of the substrate at temperatures up to the dew point of the vapor to form condensate on substantially all the particles on the substrate surface;

(d) stopping condensation on the substrate surface before the entire surface of the substrate has condensate thereon; and (e) detecting particles with condensate thereon on the substrate surface.

15. The method of claim 14 wherein the step of stopping condensation on the substrate comprises stopping condensation after condensate forms on at least some of the particles which are less than 0.1 micron in diameter, and before condensate forms in the interstices between the particles.

16. The method of claim 14 wherein the step of detecting comprises detecting by laser scanning.

17. The method of claim 14, wherein in step (b), vapor is introduced into the condensation zone so that substantially the entire surface of the substrate is contacted with the vapor simultaneously.

18. The method of claim 14, wherein in step (d), condensation of vapor on the substrate surface is stopped by removing the substrate from the condensation zone.

19. A method for detecting sub-micron sized particles on a substrate having an upper and lower surface, the method comprising the steps of:

(a) placing the lower surface of the substrate in a condensation chamber, the chamber containing a liquid having a dew point;

(b) evaporating vapor from the liquid;

(c) contacting substantially the entire upper surface of the substrate against a heat sink to maintain the lower surface of the substrate at temperatures up to the dew point of the vapor to selectively form condensate from the vapor on substantially all the particles on the lower surface of the substrate;

(d) stopping condensation of vapor on the lower surface of the substrate before the entire lower surface of the substrate has condensate thereon; and (e) detecting particles with condensate thereon on the lower substrate surface.

20. The method of claim 19 wherein the temperature of the substrate is maintained at about the dew point of the vapor.

21. The method of claim 19 wherein the step of stopping condensation of vapor comprises stopping condensation after condensate forms on at least some of the particles which are less than 0.1 micron in diameter, and before condensate forms in the interstices between the particles.

22. The method of claim 19 wherein the step of placing the substrate in the condensation chamber comprises securing the substrate in a substantially horizontal position above and spaced apart from the liquid.

23. The method of claim 19 wherein the step of detecting comprises detecting particles less than 0.1 micron in diameter by laser scanning.

24. The method of claim 19, wherein in step (b), vapor is evaporated from the liquid so that substantially the entire lower surface of the substrate is contacted with the vapor simultaneously.

25. The method of claim 19, wherein in step (d), condensation of vapor on the lower substrate surface is stopped by removing the substrate from the condensation zone.

26. An apparatus for enlarging the apparent size of particles on a surface of a substrate to facilitate detection of the particles, the apparatus comprising:

(a) a condensation chamber;

(b) a holder for holding the substrate in the chamber;

(c) a vapor source for providing vapor in the condensation chamber for contacting the surface of the substrate having particles thereon; and (d) a heat sink comprising a vacuum port for holding a sufficiently large portion of the substrate in contact with the heat sink, to maintain substantially the entire substrate surface at temperatures up to the dew point of the vapor so that condensate is selectively formed on particles on the substrate surface without condensate forming on the entire surface of the substrate.

27. The apparatus of claim 26 in which the holder holds the substrate spaced apart from and substantially parallel to the vapor source.

28. The apparatus of claim 26 in which the vapor source comprises a liquid, and a heater for heating the liquid.

29. The apparatus of claim 26 further comprising means for detecting the particles with condensate thereon on the substrate surface.

30. The apparatus of claim 29 wherein the detecting means comprises a laser scanning device.

31. A method for detecting and classifying particles on a substrate surface, the method comprising the steps of:

(a) exposing the entire substrate surface to a vapor;

(b) condensing the vapor to form condensate on some of the particles on the substrate surface by contacting the substrate against a heat sink so that the substrate surface is maintained at temperatures up to the dew point of the vapor;

(c) stopping condensation of vapor on the substrate surface after a predetermined time;

(d) detecting the particles with condensate thereon on the substrate surface; and (e) repeating steps (a) through (d) for different predetermined times to detect and classify other particles on the substrate surface.

32. The method of claim 31 further comprising the step of classifying the size of the particles on the substrate surface by comparing the different predetermined times at which step (c) was performed.

33. The method of claim 31 wherein each of the predetermined times is less than about 1 minute.

34. The method of claim 33 wherein each of the predetermined times is less than about 30 seconds.

35. The method of claim 33 wherein the substrate surface is exposed to a vapor by the steps of (i) placing the substrate in a condensation chamber having a liquid with a dew point, and (ii) vaporizing the liquid in the condensation chamber.

36. The method of claim 33, wherein in step (b), the substrate is contacted against the heat sink using a vacuum.

37. The method of claim 31, wherein in step (a), the entire surface of the substrate is exposed to the vapor simultaneously.

38. A method for detecting particles on a surface of a substrate comprising the steps of:

(a) exposing a heat sink to about room temperature;

(b) maintaining substantially the entire surface of the substrate at about room temperature by holding a sufficiently large portion of the substrate against the heat sink using a vacuum;

(c) introducing vapor in a condensation zone, the vapor formed by heating a liquid to above room temperature;

(d) exposing the entire surface of the substrate to the vapor in the condensation zone to selectively form condensate on substantially all the particles on the substrate surface;

(e) stopping condensation of vapor on the substrate surface before the entire surface of the substrate has condensate thereon by removing the substrate from the condensation zone; and (f) detecting the particles with condensate thereon on the substrate surface.

39. An apparatus for enlarging the apparent size of particles on a lower surface of a substrate to facilitate detection of the particles, the apparatus comprising:

(a) a condensation chamber having a metallic lid;

(b) a vapor source for providing vapor in the condensation chamber; and (c) a holder for holding a sufficiently large portion of an upper surface of the substrate to the metallic lid in the condensation chamber, so that the metallic lid serves as a heat sink to maintain substantially the entire lower surface substrate at temperatures up to the dew point of the vapor to selectively form condensate on particles on the lower surface of the substrate without forming condensate on the entire substrate surface.

* * * * *